US008536334B2

(12) United States Patent  
Sajitz et al.

(10) Patent No.: US 8,536,334 B2  
(45) Date of Patent: Sep. 17, 2013

(54) METHOD FOR PRODUCING 3,7-DIAZA-BICYCLO[3.3.1]NONANE METAL COMPLEXES

(75) Inventors: Melanie Sajitz, Plettenbeger (DE); Barbara Duecker, Mainz (DE); Michael Wessling, Kandern (DE)

(73) Assignee: Clariant Finance (BVI) Limited, Tortola (VG)

( * ) Notice: Subject to any disclaimer, the term of this patent is extended or adjusted under 35 U.S.C. 154(b) by 246 days.

(21) Appl. No.: 13/140,589

(22) PCT Filed: Dec. 12, 2009

(86) PCT No.: PCT/EP2009/008907  
§ 371 (c)(1), (2), (4) Date: Jul. 13, 2011

(87) PCT Pub. No.: WO2010/069524  
PCT Pub. Date: Jun. 24, 2010

(65) Prior Publication Data  
US 2011/0263857 A1 Oct. 27, 2011

(30) Foreign Application Priority Data

Dec. 19, 2008 (DE) .......................... 10 2008 064 009  
Dec. 12, 2009 (WO) ................. PCT/EP2009/008907

(51) Int. Cl.  
*C07F 15/02* (2006.01)  
*C07F 15/00* (2006.01)

(52) U.S. Cl.  
USPC ............................................... 546/10; 546/2

(58) Field of Classification Search  
USPC ...................................................... 546/10, 2  
See application file for complete search history.

(56) References Cited

U.S. PATENT DOCUMENTS

| 3,532,634 | A | 10/1970 | Woods |
| 4,414,127 | A | 11/1983 | Fu |
| 4,626,373 | A | 12/1986 | Finch et al. |
| 6,734,155 | B1 | 5/2004 | Herbots et al. |
| 6,875,734 | B2 | 4/2005 | Reinhardt et al. |
| 7,094,745 | B2 | 8/2006 | Jonas et al. |
| 8,148,530 | B2 | 4/2012 | Wessling et al. |
| 2003/0162681 | A1 | 8/2003 | Hage et al. |
| 2011/0146723 | A1 | 6/2011 | Reinhardt et al. |
| 2011/0152528 | A1 | 6/2011 | Sajitz et al. |
| 2011/0166055 | A1 | 7/2011 | Reinhardt et al. |

FOREIGN PATENT DOCUMENTS

| DE | 44 43 177 | 6/1996 |
| DE | 19909546 | 6/2000 |
| DE | 102005027619 | 12/2006 |
| EP | 0 072 166 | 2/1983 |
| EP | 0 082 563 | 6/1983 |
| EP | 0 141 470 | 5/1985 |
| EP | 0 157 483 | 10/1985 |
| EP | 0 237 111 | 9/1987 |
| EP | 0765381 | 12/1995 |
| EP | 0909809 | 4/1999 |
| EP | 1 445 305 | 8/2004 |
| EP | 1 520 910 | 4/2005 |
| WO | WO 95/34628 | 12/1995 |
| WO | WO 01/45842 | 6/2001 |
| WO | WO 02/48301 A1 | 6/2002 |
| WO | WO 02/068574 A1 | 9/2002 |
| WO | WO 03/104234 A1 | 12/2003 |
| WO | WO 2005/112631 | 12/2005 |

OTHER PUBLICATIONS

International Search Report for PCT/EP2006/005582 dated Oct. 12, 2006.  
Translation of International Preliminary Report on Patentability for PCT/EP2006/005582, dated Jan. 16, 2008.  
International Search Report for PCT/EP2009/008907 dated Mar. 26, 2010.  
Translation of International Preliminary Report on Patentability for PCT/EP2009/008907, Jun. 21, 2011.  
International Search Report for PCT/EP2009/005937 dated Dec. 4, 2009.  
Translation of International Preliminary Report on Patentability for PCT/EP2009/005937, dated May 12, 2011.  
Borzel, Heidi, et al, "Iron coordination chemistry with tetra-, penta-andhexadentate bispidine-type ligands", Inorganica Chimica Acta, 337(2002), pp. 407-419.  
Siener, Tom et al: "Synthesis and Opioid Receptor Affinity of a Series of 2,4-Diaryl- Substituted 3,7-Diazabicyclononanones", Journal of Medicinal Chemistry , 43(2000), pp. 3746-3751, Sep. 13, 2000.  
Seifen-Öle-Fette-Wachse, vol. 116, No. 20/1990" on pp. 805-808.  
T.H. Bennur et al., Journal of Molecular Catalysis A: Chemical 185 (2002) 71-80).  
Eur. J. Org. Chem. (2008) 1019-1030.  
International Search Report for PCT/EP2009/006163 dated Nov. 20, 2009.  
Translation of International Preliminary Report on Patentability for PCT/EP2009/006163, May 26, 2011.  
International Search Report for PCT/EP2009/006162 dated Nov. 10, 2009.  
Translation of International Preliminary Report on Patentability for PCT/EP2009/006162, May 26, 2011.  
A. Huizing et al., Mat. Res. Bull. vol. 12, pp. 605-6166, 1977.  
B. Donkova et al., Thermochimica Acta, vol. 421, pp. 141-149, 2004.  
English Abstract for DE 44 43 177, dated Jun. 13, 1996.  
English Abstract for DE19909546, dated Jun. 29, 2000.

*Primary Examiner* — Charanjit Aulakh  
(74) *Attorney, Agent, or Firm* — Tod A. Waldrop

(57) ABSTRACT

The invention relates to a method for producing 3,7-diaza-bicyclo[3.3.1]nonane metal complexes, wherein the ligand, a 3,7-diaza-bicyclo[3.3.1]nonane compound, is reacted with an aqueous metal(II)salt solution in one step. According to the invention, the reaction stage is carried out with water as solvent.

8 Claims, No Drawings

METHOD FOR PRODUCING 3,7-DIAZA-BICYCLO[3.3.1]NONANE METAL COMPLEXES 3,7-Diazabicyclo[3.3.1]nonane ligands of the formula (1) are interesting compounds for various applications. Inter alia, their transition metal complexes are very effective bleach and oxidation catalysts.

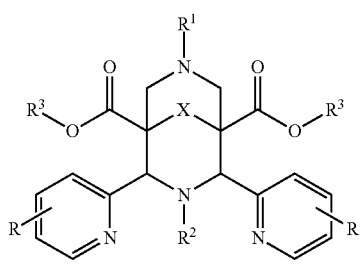

(1)

Their use as bleach catalyst in detergents and cleaners is claimed inter alia in WO 02/48301, US 2003/0 162 681 and WO 03/104 234.

The production of these iron complexes is described inter alia in Inorg. Chimica Acta, 337 (2002) 407-419 on a laboratory scale. Patent applications such as EP 0765381, EP 0909809 and WO 02/48301 likewise show the synthesis of these metal complexes.

These known syntheses take place by reacting the particular ligand with a metal salt in an organic solvent such as acetonitrile. The process is carried out under argon or nitrogen and anhydrous conditions. The yields here are only moderate and lie between 40 and 70%. For isolating the end product, the described synthesis method requires high solvent additions for the purification, such as e.g. methanol, acetic ester, acetone or dichloromethane. The choice of solvents and the strictly anhydrous conditions (anhydrous solvents, argon or nitrogen blanketing of the reaction) lead to problems and an increase in cost in the case of reaction on an industrial scale.

The object of the present invention is to find an improved and simplified method for producing these metal complexes. Surprisingly, it has now been found that the reaction of ligand and metal salt can be carried out in aqueous solution or suspension, giving the desired metal complexes in high yields and purities.

The invention therefore provides a method for producing 3,7-diazabicyclo[3.3.1]nonane metal complexes of the formula (2)

$$[M_aL_kZ_n]Y_m \quad (2)$$

in which M represents the following metals: Mn(II)-(III)-(IV), Cu(I)-(II)-(III), Fe(II)-(III)-(IV)-(V) and Co(I)-(II)-(II);

L is a ligand of the formula (1) or its protonated or deprotonated form, where R can be hydrogen, hydroxyl, $C_1$-$C_4$-alkyl; $R^1$ can be $C_1$-$C_4$-alkyl, $C_6$-$C_{10}$-aryl, pyridinyl-$C_1$-$C_4$-alkyl, $(CH_2)_{n1}N(CH_3)_2$ (n1 is preferably 1-10); $R^2$ can be $C_1$-$C_4$-alkyl, $C_6$-$C_{10}$-aryl; $R^3$ can be $C_1$-$C_4$-alkyl, X can be C=O or $C(OH)_2$,

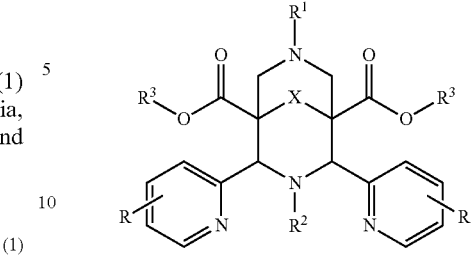

(1)

Z is a coordinating compound selected from mono-, bi- or tri-charged anions or neutral molecules which can coordinate to a metal in mono-, bi- or tri-dentate form, such as e.g.: $OH^-$, $NO_3^-$, NO, $S^{2-}$, $RS^-$, $PO_4^{3-}$, $H_2O$, $CO_3^{2-}$, ROH, $Cl^-$, $Br^-$, $CN^-$, $ClO_4^-$, $RCOO^-$, $SO_4^{2-}$;

Y is an anion balancing the charge of the complex;
a is an integer from 1 to 10, preferably from 1 to 4;
k is an integer from 1 to 10;
n is an integer from 1 to 10, preferably from 1 to 4;
m is an integer from 1 to 20, preferably from 1 to 8.

The counterion Y in formula (2) balances out the charge z of the complex which arises through the ligands L, the metal M and the coordinating species Z.

Preferred counterions are e.g. $RSO_4^-$, $SO_4^{2-}$, $NO_3^-$, $Cl^-$, $Br^-$, $I^-$, $ClO_4^-$, $BF_4^-$, $PF_6^-$, $RSO_3^-$.

The method according to the invention very generally consists in dissolving or suspending, preferably suspending, the ligand in water, and complexing it with a metal salt. The metal salt contains a metal M as metal and an anion Y as anion. The metal salt used is preferably a metal(II) salt and particularly preferably Fe(II) chloride. Particular preference is given to producing the compound iron (1+), chloro[dimethyl 9,9-dihydroxy-3-methyl-2,4-di(2-pyridinyl-κN)-7-[(2-pyridinyl-κN)methyl]-3,7-diazabicyclo[3.3.1]nonane-1,5-dicarboxylate-κN3, κn7]-, chloride (1:1).

For complexing the ligand L, the metal salt is preferably added to the aqueous solution or suspension of the ligand L either in the form of a solid or in the form of an aqueous metal salt solution.

The method according to the invention is preferably carried out at room temperature.

The synthesis preferably takes place by suspending the ligand (1) in water within 30 to 60 minutes with vigorous mixing and, with stirring, admixing it with an equimolar amount of aqueous iron(II) salt solution with a concentration of preferably 30% by weight of Fe(II) salt. The weight ratio of water to ligand during the dissolution process here is approximately 4:1 to 1:1, preferably 1.6:1. The molar ratio of ligand to iron(II) salt is ca. 0.9:1.2 to 1.2:0.9, preferably 1:1.05. After being stirred for 3 to 5 hours at room temperature, the solution is isolated by spray granulation or filtration and drying. The yield is ca. 98% with a purity of 95-98%.

The method according to the invention takes place in water. With the method according to the invention, a higher yield is achieved compared to the methods according to the prior art. Moreover, by dispensing with organic solvents, the method according to the invention operates in a considerably more cost-effective manner.

The examples below serve to illustrate the invention in more detail without limiting it thereto.

EXAMPLES

Example 1

33.6 kg (2000 mol) of water and 20.6 kg (40 mol) of 2,4-di(2-pyridyl)-3-methyl-7-(pyridin-2-ylmethyl)-3,7-diazabicyclo[3.3.1]nonan-9-one 1,5-dimethyldicarboxylate (N2Py3o) were charged to a reaction vessel and stirred to give a homogeneous solution within 30 minutes. The reaction vessel was closed and filled with nitrogen. After rendering it inert with nitrogen, 17 kg (40.6 mol) of aqueous iron(II) chloride solution (30.2% strength) were added over the course of 30 minutes and the dropping funnel was rinsed with 5 kg of water. The reaction solution was stirred at room temperature for five hours and then dried, preferably by means of spray-drying methods. In this way, the compound with the name iron (1+), chloro[dimethyl 9,9-dihydroxy-3-methyl-2,4-di(2-pyridinyl-κN)-7-[(2-pyridinyl-κN)methyl]-3,7-diazabicyclo[3.3.1]nonane-1,5-dicarboxylate-κN3, κN7]-, chloride (1:1) was obtained.

The product was obtained as a yellow powder in a purity of >95% (HPLC) and a yield of 28.2 kg (98%).

Example 2

64.45 g (0.125 mol) of the same 3,7-diazabicyclo[3.3.1]nonane compound as in example 1 were pulverized and suspended in this form in 107.5 g (5.97 mol) of water. 52.28 g of a 30.2% strength iron(II) chloride solution were then added and the reaction mixture was stirred for three hours at room temperature. The fine suspension of the product was then converted to a pulverulent yellow end product by filtration and drying in a vacuum drying cabinet. In this way, the same product as in example 1 was obtained in a yield of 81 g (98%) with a purity of >95% (HPLC).

The invention claimed is:

1. A method for producing 3,7-diazabicyclo[3.3.1]nonane metal complexes of the formula (2)

$$[M_a L_k Z_n] Y_m \quad (2)$$

wherein
M is selected from the group consisting of the following metals: Mn(II)-(III)-(IV), Cu(I)-(II)-(III), Fe(II)-(III)-(IV)-(V) and Co(I)-(II)-(III);
L is a ligand of the formula (1) or its protonated or deprotonated form, wherein R is hydrogen, hydroxyl, or $C_1$-$C_4$-alkyl; $R^1$ is $C_1$-$C_4$-alkyl, $C_6$-$C_{10}$-aryl, pyridinyl-$C_1$-$C_4$-alkyl, or $(CH_2)_{n1}N(CH_3)_2$ wherein n1 is 1-10; $R^2$ is $C_1$-$C_4$-alkyl, or $C_6$-$C_{10}$-aryl; $R^3$ is $C_1$-$C_4$-alkyl, X is CO=O or $C(OH)_2$,

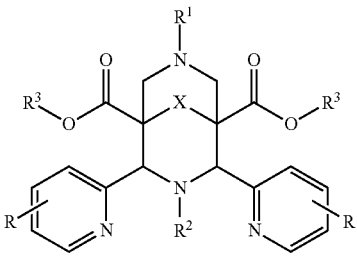

(1)

Z is a coordinating compound selected from mono-, bi- or tri-charged anions or neutral molecules which can coordinate to a metal in mono-, bi- or tri-dentate form;
Y is an anion balancing the charge of the complex;
a is an integer from 1 to 10,
k is an integer from 1 to 10;
n is an integer from 1 to 10,
m is an integer from 1 to 20,
wherein the method comprises dissolving or suspending the ligand L in water and complexing it with a metal salt.

2. The method as claimed in claim 1, wherein the metal salt is Fe(II) chloride.

3. The method as claimed in claim 1, wherein iron(1+), chloro[dimethyl 9,9-dihydroxy-3-methyl-2,4-di(2-pyridinyl-N)-7-[(2-pyridinyl-N)methyl]-3,7-diazabicyclo[3.3.1]nonane-1,5-dicarboxylate-N3, N7]-, chloride is produced.

4. The method as claimed in claim 1, wherein the metal salt for complexing the ligand L is a solid or in the form of an aqueous metal salt solution.

5. The method as claimed in claim 1, wherein the method is carried out at room temperature.

6. The method as claimed in claim 1, wherein a is an integer from 1 to 4.

7. The method as claimed in claim 1, wherein n is an integer from 1 to 4.

8. The method as claimed in claim 1, wherein m is an integer from 1 to 8.

* * * * *